(12) United States Patent
Korpinen et al.

(10) Patent No.: US 7,885,000 B2
(45) Date of Patent: Feb. 8, 2011

(54) APPARATUS FOR IMAGING CELLS

(75) Inventors: Juha Korpinen, Nokia (FI); Jussi Tarvainen, Tampere (FI)

(73) Assignee: Chip-Man Technologies Oy, Tampere (FI)

( * ) Notice: Subject to any disclaimer, the term of this patent is extended or adjusted under 35 U.S.C. 154(b) by 441 days.

(21) Appl. No.: 11/628,990

(22) PCT Filed: Jul. 8, 2005

(86) PCT No.: PCT/FI2005/050276
§ 371 (c)(1),
(2), (4) Date: Dec. 8, 2006

(87) PCT Pub. No.: WO2006/005810
PCT Pub. Date: Jan. 19, 2006

(65) Prior Publication Data
US 2008/0266653 A1    Oct. 30, 2008

(30) Foreign Application Priority Data
Jul. 9, 2004  (FI) .................................. 20040970

(51) Int. Cl.
G02B 21/34 (2006.01)
G01N 21/01 (2006.01)
(52) U.S. Cl. .................. 359/398; 359/391; 359/395
(58) Field of Classification Search .............. 359/396, 359/398, 391, 395
See application file for complete search history.

(56) References Cited

U.S. PATENT DOCUMENTS

| | | | |
|---|---|---|---|
| 4,629,862 A * | 12/1986 | Kitagawa et al. | ............ 219/200 |
| 5,106,584 A | 4/1992 | Funakubo et al. | |
| 5,870,222 A * | 2/1999 | Yamamoto et al. | .......... 359/368 |
| 6,008,010 A | 12/1999 | Greenberger et al. | |
| 6,166,761 A | 12/2000 | Arav | |
| 6,271,022 B1 | 8/2001 | Bochner | |
| 2003/0134269 A1 | 7/2003 | Hirai et al. | |
| 2004/0064013 A1 | 4/2004 | Attias | |
| 2004/0126876 A1 | 7/2004 | Ravin et al. | |
| 2004/0191754 A1 | 9/2004 | Meir et al. | |
| 2004/0265831 A1 | 12/2004 | Arav et al. | |

FOREIGN PATENT DOCUMENTS

| | | |
|---|---|---|
| JP | 2003021628 A | 1/2003 |
| JP | 2003093041 A1 | 4/2003 |
| WO | WO 9831150 A1 | 7/1998 |
| WO | WO 2004003131 A2 | 1/2004 |
| WO | WO-2004/033615 A1 | 4/2004 |

OTHER PUBLICATIONS

-PCT/ISA/210—International Search Report.
Finnish Search Report and Office Action w/ English Translation - Apr. 7, 2005.

* cited by examiner

*Primary Examiner*—Joshua L Pritchett
(74) *Attorney, Agent, or Firm*—Venable LLP; Eric J. Franklin

(57) ABSTRACT

An apparatus for imaging cells including a culture chamber, in which a cultivation sub-structure is placed, imaging optics, and actuators for providing the relative movement of the cultivation substructure and the imaging optics in such a way that the imaging optics is used to image different sites in the substructure. The cultivation substructure is isolated as a subchamber of its own that is separate from the culture chamber, and imaging is carried out by moving the imaging optics and the subchamber in relation to each other.

6 Claims, 2 Drawing Sheets ated substructure is placed, imaging optics, and actuators for providing the relative movement of the cultivation substructure and the imaging optics in such a way that the imaging optics is used to image different sites in the cultivation substructure.

APPARATUS FOR IMAGING CELLS

CROSS-REFERENCE TO RELATED APPLICATIONS

This application claims priority to Finnish patent application 20040970 filed 9 Jul. 2004 and is the national phase of PCT/FI2005/050276.

Field of the Invention

The invention relates to an apparatus for imaging cells, comprising a culture chamber, in which a cultivation substructure is placed, imaging optics, and actuators for providing the relative movement of the cultivation substructure and the imaging optics in such a way that the imaging optics is used to image different sites in the cultivation substructure.

Background of the Invention

Cell cultures are generally used e.g. in various cytobiological and biomedical analyses. Typically, the cell material to be analyzed is cultured in a Petri dish or on a well plate placed in suitable conditions with respect to the temperature, ambient gas and illumination. At various stages of the analyses, the samples are subjected to, for example, microscopy, and in arrangements of prior art, the well plate is arranged to be examined with a microscope which may be equipped with a camera. In many studies, the same samples are examined at regular intervals so that the development of the cell can be monitored.

From patent documents, a number of apparatuses are known which have been constructed in such a way that cells to be cultured in a substructure, for example in a well plate, can be kept in desired culturing environment (temperature, culture medium, atmosphere). To monitor the development of cells, for example their growth and/or the way in which they are affected by given substances added in the culture medium, it is necessary to take images at different sites of the cultivation substructure in such a way that the same sites (for example, separate wells) are imaged at regular intervals according to a given schedule.

In the simplest form, the imaging is carried out by taking the cultivation substructure out of the culturing chamber (e.g. incubator) and placing it onto a particular microscope base where the imaging can be carried out automatically, manipulators moving the base with respect to the objective of the microscope. The images thus taken are recorded in a memory and they can be processed later on. In a more automated version, the cultivation substructures are automatically removed from the incubator to be imaged according to a predetermined program, and an apparatus for implementing this is presented e.g. in U.S. Pat. No. 5,106,584.

The removal of the cultivation substructures from the incubator for imaging is a disturbing factor, because the cultivation substructure is removed from the environment where the conditions have been adjusted to be optimal, and it may be subjected to bumps when it is being moved from one base to another. Therefore, apparatuses are also known for carrying out the imaging when the cultivation substructure is in the incubator. For example, U.S. Pat. No. 6,271,022 discloses an apparatus in which the imaging is arranged inside the incubator in such a way that substructures placed on shelves on top of each other can be imaged one after the other, although accurate imaging is not achieved by this method.

U.S. Pat. No. 6,008,010 presents an apparatus in which a well plate is placed on top of the transparent bottom of a closed incubator chamber. The cover of the incubator chamber is transparent as well, wherein imaging can be performed through the incubator chamber by using a manipulator to move the whole chamber in relation to the imaging optics. With this system, it is already possible to perform imaging in situ without removing the cultivation substructure from the chamber. However, a problem lies in the fact that the whole culture chamber must be moved. Because of this, the culture chamber, or "biochamber", has been made relatively small (length×width×height 6"×5"×2"). Moreover, the use of a transparent extra plate under the bottom of the well plate is problematic for high magnifications, because the objective must be brought very close to the object.

SUMMARY OF THE INVENTION

It is an aim of the invention to eliminate the above-identified drawbacks and to present an apparatus for imaging without a need to move the whole culture chamber, so that it is possible to make the culture chamber large and, for example, very photoisolating and/or thermally insulating, and, on the other hand, to make the movable part light-weight and well transparent to light and such that various illuminating and optics systems can be brought close to the object to be imaged. To achieve this aim, the apparatus according to the invention is primarily characterized in that the cultivation substructure is isolated from the culture chamber to form a separate subchamber of its own, and imaging is carried out by moving the imaging optics and the sub-chamber in relation to each other. The imaging can be implemented, for example, in such a way that the imaging optics is placed in its position in the culture chamber, and the subchamber is moved within the culture chamber in relation to the imaging optics, or the imaging optics is arranged to be movable within the culture chamber, the subchamber remaining in its position.

The subchamber is produced most preferably by closing the cultivation substructure with a lid which hermetically seals the air space above the different sites of the cultivation substructure, isolating it as a culture environment of its own that is separate from the subchamber. Such an environment can be supplied with a desired gas composition by providing a gas inlet and a gas outlet. The gas can be exchanged by feeding desired gas into the subchamber.

The subchamber can be formed, for example, by a lid closing a well plate from above, the lid being provided with an inlet and an outlet for the gas, so that a closed air space, shared by all the wells and having a desired gas composition above the different sites (wells) of this cultivation substructure, is formed. This idea is disclosed in more detail in the parallel patent application "A substructure for cultivating cells and its use" filed simultaneously with the present application.

BRIEF DESCRIPTION OF THE DRAWING

In the following, the invention will be described in more detail with reference to the appended drawings, in which.

DETAILED DESCRIPTION OF EMBODIMENTS OF THE INVENTION

Figure 1:
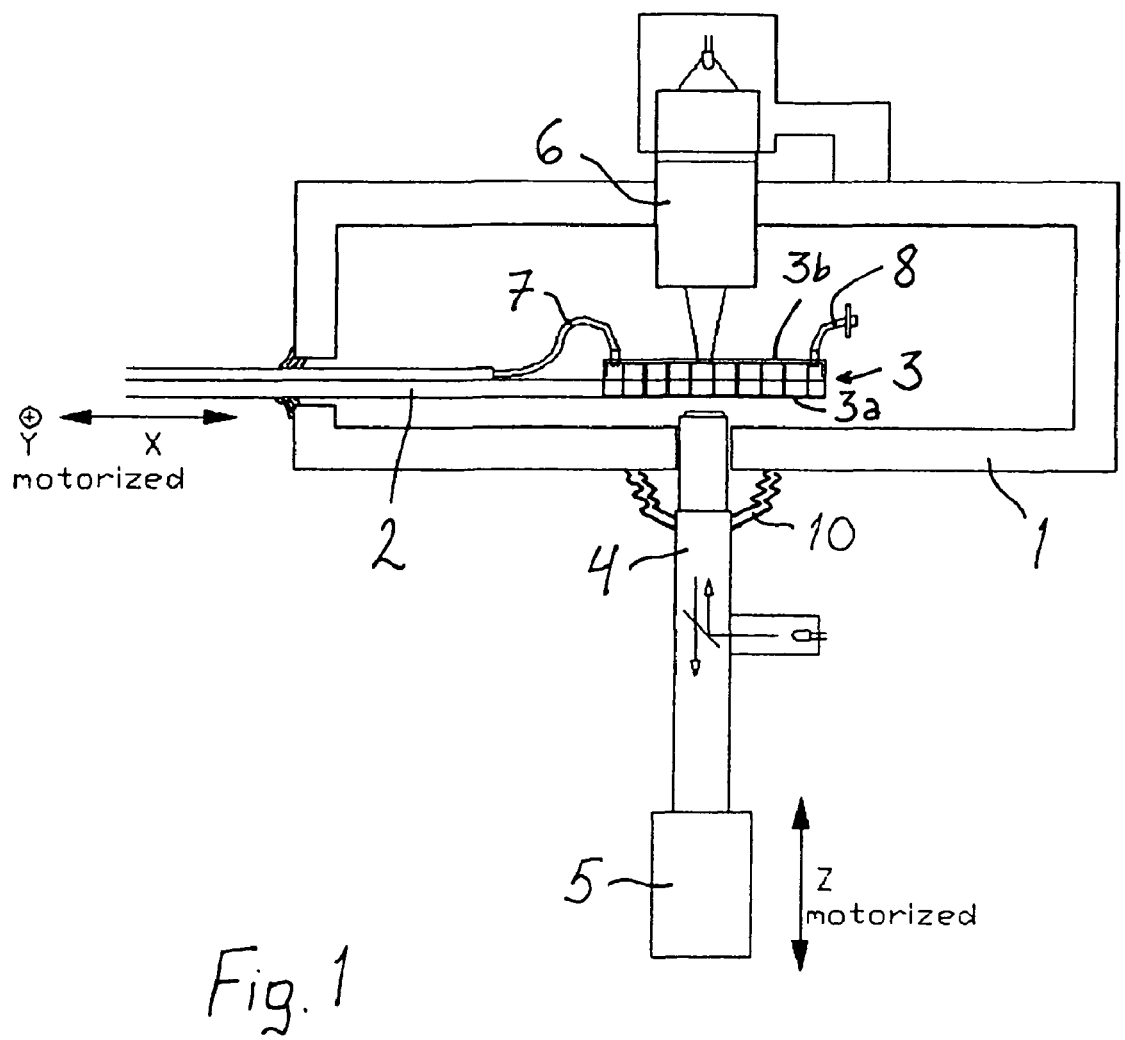
FIG. 1 shows a first embodiment of the invention.

FIG. 1 shows the first embodiment of the invention, in which a cultivation substructure is moved in a culture chamber. Inside the culture chamber 1, a subchamber 3 is arranged to be movable by means of a manipulator arm 2 moving in the X-Y plane. The subchamber is formed in this case by a well plate used as the cultivation substructure and a lid sealing it tightly from above. The bottom 3a of the subchamber 3 (the bottom 3a of the well plate) and the lid 3b are transparent so that microscopic imaging of living cells on the cultivation substructure can be carried out according to the general principle by illuminating the culture site from the direction opposite to the objective of the microscope, from above in the figure, but the structure also makes it possible to provide illumination from below, or at an angle from below, in the direction of the objective. The manipulator arm comprises an opening in which the subchamber 3 can be fixed so that the bottom 3a is freely accessible for imaging. In the figure, reference numeral 4 indicates a microscope, which is arranged to be movable, together with a digital camera 5, by means of a motor in direction Z perpendicular to the X-Y plane of moving of the cultivation substructure. The microscope is a tube microscope, and focusing can be performed by moving the combination of the tube microscope and the camera in the Z direction. Reference numeral 6 indicates an illuminator device to provide illumination in the opposite direction (from above). The illuminator device 6 is fixed to the top wall of the chamber 1.

The culture chamber 1 constitutes a dark chamber protected from ambient light, and its temperature can also be adjusted to a desired level irrespective of the ambient temperature. Heating can be provided, for example, by means of resistance plates in the walls, and the dropping of the temperature by, for example, Peltier elements. The arm 2 is introduced via a lead-through slot in the side of the chamber, sealed with e.g. elastic means so that no light or heat can enter through the slot but the arm 2 can move in the slot.

The microscope 4 is also introduced into the culture chamber 1 via a sealed opening (sealing ring 10). FIG. 1 shows how the objective can be brought close to the subchamber 3 through the bottom of the culture chamber 1. The bellows-like seal ring 10 also allows the movement of the microscope 4 in the Z direction.

The subchamber 3, in turn, is isolated from the conditions in the culture chamber 1 in such a way that it can be provided with a desired gas composition, irrespective of the gas composition in the interior of the culture chamber 1. Reference numerals 7 and 8 in the figure indicate the inlet and outlet ducts to and from the subchamber 3, respectively. The outlet duct 8 comprises a valve which lets the gas flow in one direction only, away from the subchamber 3.

Imaging is performed in the normal way, one culture site of the sub-structure (one well of the well plate) at a time, wherein several sites of a single well can be imaged. The culture site to be imaged is determined by means of the manipulator moving the subchamber 3 in the X-Y plane. Furthermore, in each culture site it is possible to take images in different planes in the Z direction by moving the microscope in a direction perpendicular to the X,Y plane, for example to take a series of images of the same culture site in different focusing planes. During the imaging, the illumination can be provided by using illumination whose duration is set accurately with a system presented in more detail in a parallel patent application "An illumination system for a microscope" filed simultaneously.

The bottom 3a of the subchamber consists of the transparent bottom of an ordinary well plate which is visible from below in the opening of the manipulator arm 2. Consequently, there is no isolating structure between the objective of the microscope 4 and the bottom of the well plate, because the objective of the microscope 4 is placed in the culture chamber 1. The objective comes close to the object, and desired optics can be used.

When the imaging is carried out from the side of the bottom of the sub-chamber 3 (well plate), the objective of the microscope comes close to the object through the transparent bottom of the well plate, for example at a distance of less than 1 mm. Thus, it is possible to use phase contrast imaging with high magnifications.

The alternatives relating to the storage and processing of the image itself do not fall within the scope of the present invention, and they will thus not be disclosed in more detail.

In the embodiment of FIG. 1, the motor moving the subchamber 3 in the X-Y plane is outside the culture chamber 1. Similarly, the camera 5 and the focusing motor of the microscope (Z direction) are outside the culture chamber 1. The culture chamber can be made small so that the volume to be heated is small and can be quickly adjusted to a given temperature.

Figure 2:
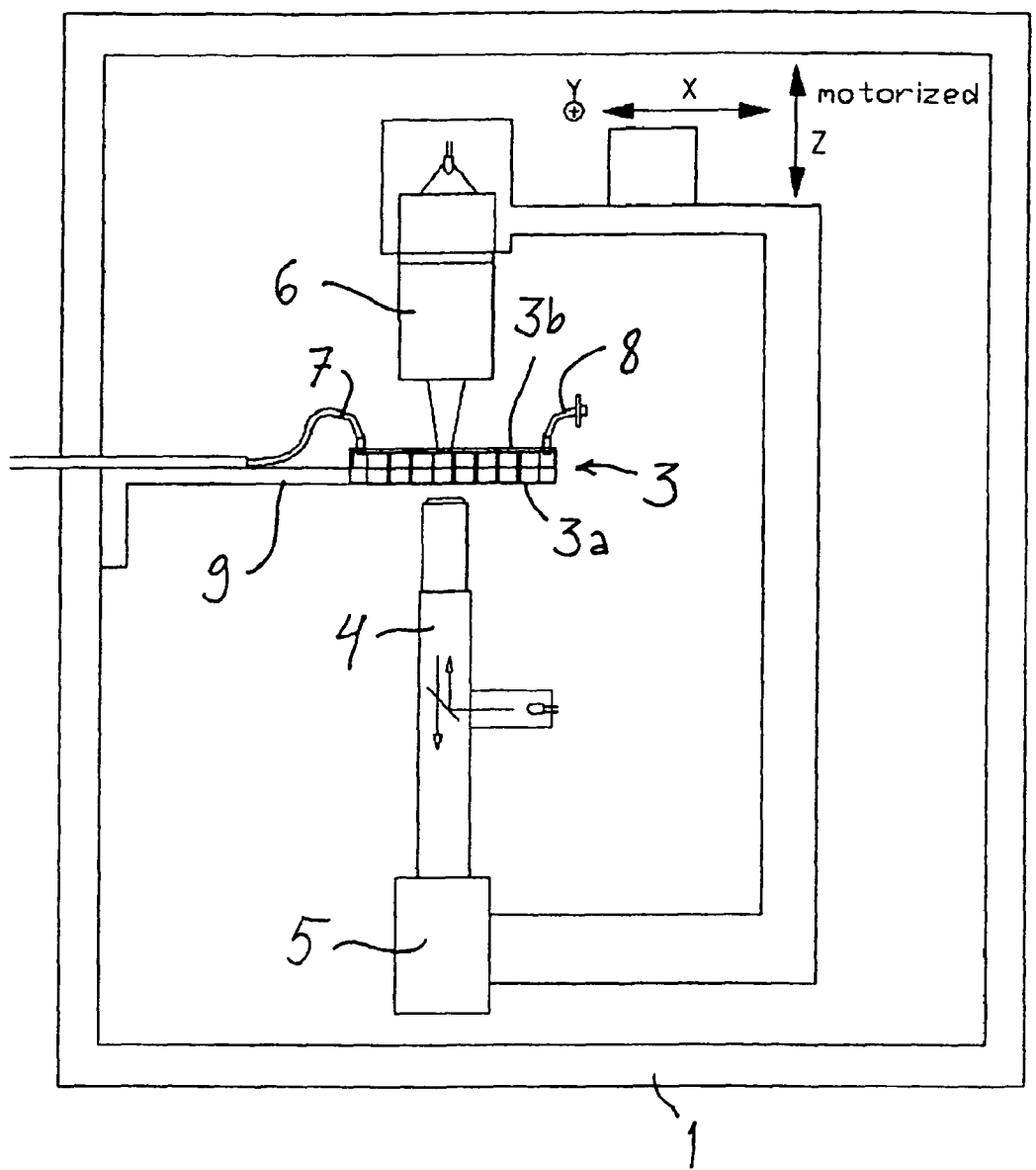
FIG. 2 shows a second embodiment of invention.

FIG. 2 shows a second embodiment in which the same reference numerals as in FIG. 1 are used to indicate parts operating in a corresponding way. The difference herein is that the subchamber 3 is placed in a fixed position in a support 9 mounted in the wall of the culture chamber 1 and comprising a fixing opening that leaves the bottom 3a of the subchamber freely accessible from below in the same way as in the manipulator arm 2. The imaging optics (the microscope 4 and the illuminator device 6) constitute a portal structure which is movable in relation to the subchamber 3 in the X, Y and Z directions and is placed entirely inside the chamber 1. Also in this embodiment it has been possible to bring the objective of the tube microscope close to the object (subchamber 3), because the whole microscope is now inside the culture chamber 1. Also in this embodiment it has been possible to bring the objective of the tube microscope close to the object (subchamber 3), because the whole microscope is now inside the culture chamber 1. Also in this embodiment, the movement of the cells has been minimized.

The invention claimed is:

1. An apparatus for imaging cells, comprising:
   a culture chamber comprising a heater configured to adjust a temperature of the culture chamber;
   a separate cultivation substructure comprising a subchamber placed in the culture chamber, the subchamber being isolated from conditions in the culture chamber such that the subchamber can be provided with a desired gas composition;
   imaging optics comprising a microscope having an objective, a focusing motor and a camera;
   actuators for providing the relative movement of the cultivation substructure and the imaging optics in such a way that different sites of the substructure are imaged by the imaging optics by moving the imaging optics and the subchamber in relation to each other;
   said subchamber being arranged movable inside the culture chamber in relation to the imaging optics for imaging said different sites of the substructure;
   the objective of the microscope of the imaging optics being introduced into the culture chamber from outside the culture chamber through a sealed opening such that the focusing motor and the camera are outside of the culture chamber; and
   the subchamber being arranged movable by a manipulator arranged outside the culture chamber,
   wherein the manipulator comprises an arm, said arm being introduced into the culture chamber via a lead-through slot on one side of the culture change, and wherein the arm comprises an opening through which the substructure is configured to be imaged.

2. The apparatus according to claim 1, wherein the subchamber is provided with gas supply and removal to adjust gas composition inside the subchamber to a desired composition, or to supply gas with a desired composition to the subchamber.

3. The apparatus according to claim 1, wherein the subchamber is provided with gas supply and removal to adjust gas composition inside the subchamber to a desired composition, or to supply gas with a desired composition to the subchamber.

4. The apparatus according to claim 1, wherein the microscope is arranged to be focused by a motor arranged outside the culture chamber.

5. The apparatus according to claim 1, wherein the manipulator is arranged to move the subchamber in a horizontal plane and the focusing motor is arranged to move the microscope in a direction perpendicular to the horizontal plane.

6. The apparatus according to claim 5, wherein a bottom of the subchamber comprises a transparent bottom of a well plate and the imaging optics are arranged to carry out imaging through the transparent bottom by the objective of the microscope below the transparent bottom.

* * * * *